(12) United States Patent
Badea

(10) Patent No.: US 7,621,277 B2
(45) Date of Patent: Nov. 24, 2009

(54) CONDOM

(76) Inventor: Daniel Badea, Triberger Weg 32, 51063 Cologne (DE)

( * ) Notice: Subject to any disclaimer, the term of this patent is extended or adjusted under 35 U.S.C. 154(b) by 171 days.

(21) Appl. No.: 11/629,898

(22) PCT Filed: Jun. 8, 2005

(86) PCT No.: PCT/EP2005/052624

§ 371 (c)(1), (2), (4) Date: Dec. 18, 2006

(87) PCT Pub. No.: WO2005/122976

PCT Pub. Date: Dec. 29, 2005

(65) Prior Publication Data

US 2008/0047564 A1 Feb. 28, 2008

(30) Foreign Application Priority Data

Jun. 18, 2004 (DE) .................. 10 2004 029 638

(51) Int. Cl.
*A61F 6/02* (2006.01)
*A61F 6/04* (2006.01)
*A61F 5/00* (2006.01)

(52) U.S. Cl. ............ 128/844; 128/842; 128/917; 128/918; 600/38

(58) Field of Classification Search ......... 128/842–845, 128/917–918; 600/38–41
See application file for complete search history.

(56) References Cited

U.S. PATENT DOCUMENTS

| 2,586,674 | A | * | 2/1952 | Lonne | 128/844 |
| 5,377,692 | A | | 1/1995 | Pfiel | |
| 5,623,945 | A | * | 4/1997 | Shecterle et al. | 128/842 |
| 2002/0022760 | A1 | | 2/2002 | Orten | |
| 2004/0006291 | A1 | * | 1/2004 | Rehrig | 601/70 |
| 2008/0188709 | A1 | * | 8/2008 | Gil | 600/38 |

FOREIGN PATENT DOCUMENTS

| DE | 100 65 006 A1 | 2/2001 |
| DE | 203 11 823 U1 | 9/2003 |

\* cited by examiner

*Primary Examiner*—Patricia M Bianco
*Assistant Examiner*—Brandon Jackson
(74) *Attorney, Agent, or Firm*—Miles & Stockbridge P.C.; David R. Schaffer, Esq.

(57) ABSTRACT

The invention relates to a condom (10) for the penis. The condom (10) comprises a flexible condom wall (12). In the condom wall plane a shaft channel (18) is arranged in which a flexible rotary shaft (16) is supported. The rotary shaft (16) is adapted to be driven by a rotary drive. The rotating shaft (16) generates stimulating vibrations.

23 Claims, 1 Drawing Sheet

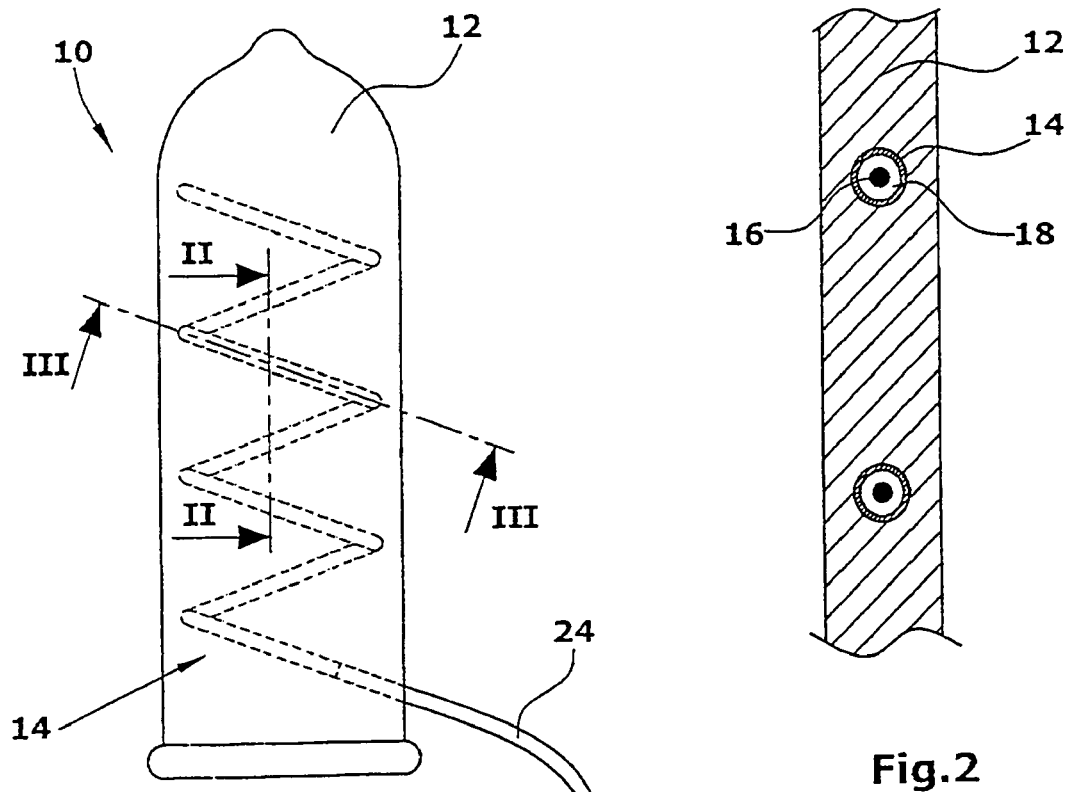
Fig.1
Fig.2
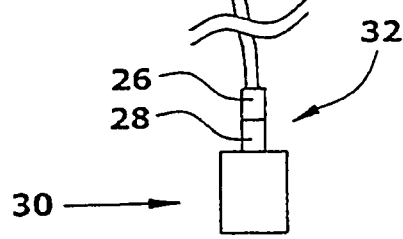
Fig.3

CONDOM

CROSS REFERENCE TO RELATED APPLICATIONS

This application claims the benefit of International Application No. PCT/EP2005/052624, filed Jun. 8, 2005, which claims the benefit of and priority to German Application No. 10 2004 029 638.3, filed Jun. 18, 2004, all of which are incorporated herein by reference in their entirety.

BACKGROUND OF THE INVENTION

The invention relates to a condom for the penis.

Condoms are used for contraception purposes and for hygienic reasons. For stimulation purposes, the flexible condom wall may be provided with nubs, rings etc. These stimulating elements are however effective only when the condom is moved. The penis is not stimulated at all or only to a small degree.

SUMMARY OF THE INVENTION

It is an object of the invention to provide a condom with improved stimulation properties.

The condom according to the invention comprises a shaft channel located in the condom wall plane, in which channel a flexible rotary shaft is arranged. During use of the condom, the rotary shaft is driven by an oscillating or rotating rotary drive such that the shaft turns or rotates in the shaft channel located in the condom wall. In this manner, vibration is produced in the condom in the region of the shaft channel, said vibration being transmitted both to the interior of the condom and to the exterior of the condom.

The shaft channel and the shaft may be helically arranged in the condom wall plane, for example. It is however also possible to provided a plurality of shaft channels including the shaft in or at the condom wall and arranged in axial relationship, for example.

Preferably, the shaft channel is defined by a flexible tube made from a material differing from the condom wall material. For example, the condom wall may be made of latex, while the channel tube is made of plastic material.

According to a preferred embodiment, the channel tube is enclosed in the condom wall. For example, the channel tube may be sealed in the latex condom wall. Generally, it is also possible to fasten the channel tube in a different manner to the condom wall, such as by gluing or welding. In any case, the channel tube is permanently fixed to the condom wall over its overall length.

According to a preferred embodiment, the rotary shaft is defined by a flexible metal wire. The metal wire is secured against torsion such that the rotary motions performed by the rotary drive can be transmitted over a length of more than 1-2 m.

Preferably, the course of the shaft describes a plurality of sharp bends. The sharp bends ensure that the shaft in the shaft channel is eccentrically supported at the bend locations and produces a strong vibration in the bend region when the shaft rotates.

Alternatively or in addition to the sharp bends, the shaft may comprise a plurality of small eccentric massage bodies. The massage bodies together with the shaft are smaller than the shaft channel such that the shaft comprising the massage bodies can be inserted into the shaft channel. The massage bodies may be small balls, for example, which are soldered, welded or otherwise fastened to the rotary shaft.

According to a preferred embodiment, the shaft channel and/or the flexible tube extend beyond the condom wall by at least 5 cm. One longitudinal end of the shaft channel and/or the channel tube is closed, while the other longitudinal end of the shaft channel and/or the channel tube is open and continues to extend beyond the condom wall by at least 5 cm. The open end can be connected with the rotary drive. This ensures that the rotary drive is not immediately connected to the condom.

According to a preferred embodiment, the rotary shaft comprises a coupling for connecting a rotary drive. The coupling allows for rapid and simple disconnection of the rotary drive from the rotary shaft. In this manner, it is ensured that the rotary drive can be repeatedly used.

An embodiment of the invention will now be described in greater detail with reference to the drawings in which:

BRIEF DESCRIPTION OF THE DRAWINGS

FIG. 1 shows a side view of a condom according to the invention comprising a helically arranged shaft channel including a shaft.

FIG. 2 shows a longitudinal section along line II-II of a condom wall of the condom shown in FIG. 1.

FIG. 3 shows a sectional view along line III-III of the condom of FIG. 1 showing the shaft channel and the shaft in longitudinal direction.

DESCRIPTION OF THE PREFERRED EMBODIMENTS

FIG. 1 shows a condom 10 for a penis. The condom 10 essentially comprises a tubular condom wall 12, a shaft-channel tube 14 and a rotary shaft 16 arranged in the shaft-channel tube 14. The tube 14 encloses a shaft channel 18 whose inner diameter amounts to at least 1.2 times the diameter of the rotary shaft 16.

The condom wall 12 is flexible and elastic and is made of latex. The condom wall 12 may however also be made of a different material such as an elastic plastic material. The shaft-channel tube 14 is made of a plastic material having a low inside friction coefficient relative to the rotary shaft 16 such that low-friction rotation of the shaft 16 in the tube 14 is ensured. In this manner, it is guaranteed that the rotary motion of the shaft 16 is transmitted over the overall tube and/or channel length.

As shown in FIG. 2, the shaft-channel tube 14 is sealed in the latex condom wall. The tube may however also be glued, welded or otherwise fastened over its overall length to the outside or the inside of the condom wall.

The rotary shaft 16 is defined by a flexible metal wire which offers a high rigidity with regard to torsion. In this manner, it is ensured that the rotary motion is transmitted over the overall length of the shaft 16.

As shown in FIG. 3, the shaft 16 describes a plurality of sharp bends 22 over its length. Each sharp-bend angle amounts to at least 10 degrees relative to the longitudinal axis of the shaft. The sharp bends 22 are arranged at a distance of a few millimeters to each other. The sharp bends 22 cause in particular in the region of the sharp bends 22 vibration of the shaft rotary frequency to be generated by the rotary motion of the shaft 16.

As shown in FIG. 1, a connecting tube 24 extends beyond the condom wall 12 in continuation of the condom-wall tube 14. The connecting tube 24 is at least 5 cm long and comprises at its end facing away from the condom a coupling portion 26 connected with a coupling portion 28 of a rotary drive 30. The two coupling portions 26,28 form a coupling 32. The coupling 32 is easy to disconnect and to secure.

The rotary drive 30 generates a rotary motion which is transmitted to the shaft 16. When the shaft 16 rotates, corresponding vibrations, which may have a stimulating effect, are produced in particular in the region of the sharp bends 22.

Alternatively or in addition to the sharp bends 22 small massage bodies, which may also generate vibrations, may be eccentrically arranged at the shaft 16.

Although a preferred embodiment of the invention has been specifically illustrated and described herein, it is to be understood that minor variations may be made in the apparatus without departing from the spirit and scope of the invention, as defined by the appended claims.

The invention claimed is:

1. A condom (10) for the penis, comprising a flexible condom wall (12),
   characterized by
   a shaft channel (18) arranged in a condom-wall plane, and defined by a flexible tube (14) made from a material differing from the condom-wall material, and
   a rotary flexible shaft (16) in the shaft channel (18).

2. The condom (10) according to claim 1, wherein the shaft channel (18) helically extends in the condom wall.

3. A condom (10) for the penis, comprising a flexible condom wall (12),
   characterized by
   a shaft channel (18) arranged in a condom-wall plane and defined by a flexible tube (14) made from a material differing from the condom-wall material,
   a rotary flexible shaft (16) in the shaft channel (18), and
   a shaft-channel tube (14) being enclosed in the condom wall (12).

4. The condom (10) according to claim 1, characterized in that the rotary shaft (16) is defined by a flexible metal wire.

5. The condom (10) according to claim 1, characterized in that the longitudinal course of the rotary shaft (16) describes a plurality of sharp bends (22).

6. The condom (10) according to claim 1, characterized in that the rotary shaft (16) comprises a plurality of massage bodies in its longitudinal course.

7. The condom (10) according to claim 1, characterized in that a connecting tube (24) is provided which extends beyond the condom wall (12) by at least 5 cm long in continuation of the shaft channel (18).

8. The condom (10) according to claim 1, characterized in that the rotary shaft (16) comprises a coupling portion (26) for connecting to a rotary drive (30).

9. A condom (10) for the penis, comprising a flexible condom wall (12),
   characterized by
   a shaft channel (18) arranged in a condom-wall plane and defined by a flexible tube (14) made from a material differing from the condom-wall material, and
   a rotary flexible shaft (16) in the shaft channel (18),
   the shaft channel (18) being defined by a flexible tube (14) made from a material differing from the condom-wall material.

10. The condom (10) according to claim 1, characterized in that the shaft-channel tube (14) is enclosed in the condom wall (12).

11. The condom (10) according to claim 3, wherein the shaft channel (18) helically extends in the condom wall.

12. The condom (10) according to claim 3, characterized in that the rotary shaft (16) is defined by a flexible metal wire.

13. The condom (10) according to claim 3, characterized in that the longitudinal course of the rotary shaft (16) describes a plurality of sharp bends (22).

14. The condom (10) according to claim 3, characterized in that the rotary shaft (16) comprises a plurality of massage bodies in its longitudinal course.

15. The condom (10) according to claim 3, characterized in that a connecting tube (24) is provided which extends beyond the condom wall (12) by at least 5 cm long in continuation of the shaft channel (18).

16. The condom (10) according to claim 3, characterized in that the rotary shaft (16) comprises a coupling portion (26) for connecting to a rotary drive (30).

17. The condom (10) according to claim 9, wherein the shaft channel (18) helically extends in the condom wall.

18. The condom (10) according to claim 9, characterized in that the rotary shaft (16) is defined by a flexible metal wire.

19. The condom (10) according to claim 9, characterized in that the longitudinal course of the rotary shaft (16) describes a plurality of sharp bends (22).

20. The condom (10) according to claim 9, characterized in that the rotary shaft (16) comprises a plurality of massage bodies in its longitudinal course.

21. The condom (10) according to claim 9, characterized in that a connecting tube (24) is provided which extends beyond the condom wall (12) by at least 5 cm long in continuation of the shaft channel (18).

22. The condom (10) according to claim 9, characterized in that the rotary shaft (16) comprises a coupling portion (26) for connecting to a rotary drive (30).

23. The condom (10) according to claim 9, characterized in that the shaft- channel tube (14)is enclosed in the condom wall (12).

* * * * *